United States Patent
Nieda et al.

(10) Patent No.: US 8,962,313 B2
(45) Date of Patent: Feb. 24, 2015

(54) METHOD FOR THE SIMULTANEOUS INDUCTION OF CTL AND γδT CELL

(75) Inventors: Mie Nieda, Tokyo (JP); Mai Tomiyama, Tokyo (JP); Masato Muto, Tokyo (JP)

(73) Assignee: Medinet Co., Ltd., Kanagawa (JP)

( * ) Notice: Subject to any disclaimer, the term of this patent is extended or adjusted under 35 U.S.C. 154(b) by 242 days.

(21) Appl. No.: 13/001,581

(22) PCT Filed: Jun. 30, 2009
(Under 37 CFR 1.47)

(86) PCT No.: PCT/JP2009/003039
§ 371 (c)(1),
(2), (4) Date: Dec. 8, 2011

(87) PCT Pub. No.: WO2010/001599
PCT Pub. Date: Jan. 7, 2010

(65) Prior Publication Data
US 2012/0107292 A1 May 3, 2012

(30) Foreign Application Priority Data

Jul. 1, 2008 (JP) ................................ 2008-172797

(51) Int. Cl.
| C12N 5/00 | (2006.01) |
| C12N 5/0783 | (2010.01) |
| A61K 39/00 | (2006.01) |
| A61K 35/12 | (2006.01) |

(52) U.S. Cl.
CPC .......... *C12N 5/0636* (2013.01); *A61K 39/0011* (2013.01); *C12N 5/0638* (2013.01); *A61K 2035/124* (2013.01); *A61K 2039/5158* (2013.01); *A61K 2039/57* (2013.01); *C12N 2501/999* (2013.01); *C12N 2501/2302* (2013.01)
USPC ......................................... 435/325; 435/375

(58) Field of Classification Search
USPC ....................................................... 435/325
See application file for complete search history.

(56) References Cited

U.S. PATENT DOCUMENTS

| 2005/0048646 A1 | 3/2005 | Nieda et al. |
| 2005/0130899 A1 | 6/2005 | Itoh et al. |
| 2007/0190169 A1 | 8/2007 | Nieda et al. |
| 2008/0031888 A1 | 2/2008 | Itoh et al. |
| 2009/0104161 A1 | 4/2009 | Nieda et al. |
| 2010/0015169 A1 | 1/2010 | Itoh et al. |

FOREIGN PATENT DOCUMENTS

| EP | 1 462 456 | 9/2004 |
| WO | WO-03/050140 | 6/2003 |
| WO | WO-2006/006720 | 1/2006 |
| WO | WO-2007/029689 | 3/2007 |

OTHER PUBLICATIONS

Freshney, Ian. Culture of Animal Cells: A Manual of Basic Technique and Specialized Applications, Sixth Edition. Wiley-Blackwell (2010) Chapters 8 and 10.*
Master's Degree Thesis (Soochow University, Suzhou, China) of Dai Wei, entitled "Stimulation of γδ Cell in Peripheral Blood by Zolendronic Acid and its Cytotoxic Effect in Nonspecific Immunity of Hepatoma," pub date Mar. 15, 2008, 40 pages.
Makita et al., Antilung Cancer Effect of WT1-specific Cytotoxic T Lymphocytes1, Clinical Cancer Research, vol. 8, pp. 2626-2631 (2002).
Miyagawa et al., Essential Requirement of Antigen Presentation by Monocyte Lineage Cells for the Activation of Primary Human {{gamma}}{{delta}} T Cells by Aminobisphosphonate Antigen, The Journal of Immunology, vol. 166, pp. 5508-5514 (2001).
Ohminami et al., HLA class I-restricted lysis of leukemia cells by a CD8 cytotoxic T-lymphocyte clone specific for WT1 peptide, Blood, vol. 95, pp. 286-293, (Jan. 2011).
Paczesny et al., Expansion of Melanoma-specific Cytolytic CD8 T Cell Precursors in Patients with Matastatic Melanoma Vaccinated with CD34 Progenitor-derived Dendritic Cells, The Journal of Experimental Medicine, vol. 199 (11), pp. 1503-1511, (Jun. 2004).
Rivoltini et al., Induction of Tumor-Reactive CTL from Peripheral Blood and Tumor-Infiltrating Lymphocytes of Melanoma Patients by In Vitro Simulation with an Immunodominant Peptide of the Human Melanoma Antigen MART-1, The Journal of Immunology, vol. 154, pp. 2257-2265 (1995).
Takahara et al., Copulsing tumor antigen-pulsed dendritic cells with zoledronate efficiently enhance the expansion of tumor antigen-specific CD8 T cells via V9 T cell activation, Journal of Leukocyte Biology, vol. 83, 742-754, (Mar. 2008).
Tsuboi et al., Enhanced induction of human WT1-specific cytotoxic T lymphocytes with a 9-mer WT1 peptide modified at HLA-A*2402-binding residues, Cancer Immunol Immunother, Dec. 2002, vol. 51, pp. 614-620 (published online Oct. 18, 2002).
International Search Report for International Patent Application No. PCT/JP2009/003039, mailing date Sep. 1, 2009, 6 pages.
Hartmann et al., Analysis of Plasmacytoid and Myeloid Dendritic Cells in Nasal Epithelium, Clinical and Vaccine Immunology, Nov. 2006, p. 1278-1286.
Salio et al., Mature Dendritic Cells Primte Functionally Superior Melan-A-Specific CD8 Lymphocytes as Compared with Nonprofessional APC, The Journal of Immunology 2001, 167:1188-1197, 11 pages.

\* cited by examiner

*Primary Examiner* — Jon P Weber
*Assistant Examiner* — Kara Johnson
(74) *Attorney, Agent, or Firm* — Foley & Lardner LLP

(57) ABSTRACT

Disclosed are: a method for culture of disease antigen specific CTLs and γδT cells in one culture step conveniently and efficiently; and a pharmaceutical agent and a therapeutic/prophylactic method both of which use a cell produced by the method. Blood is collected and peripheral blood mononuclear cells are separated from the blood. Aminobisphosphonate and a disease antigen are added to the peripheral blood mononuclear cells at the beginning of culture, and the cell culture is carried out for a predetermined period to proliferate/induce disease antigen specific CTLs and γδT cells simultaneously until the numbers of the cells reach values that are effective for the treatment of a disease. The CTLs and the γδT cells thus produced are used for the treatment.

16 Claims, No Drawings

METHOD FOR THE SIMULTANEOUS INDUCTION OF CTL AND γδT CELL

CROSS-REFERENCE TO RELATED PATENT APPLICATIONS

This patent application is a national stage of International Patent Application No. PCT/JP2009/003039, filed Jun. 30, 2009, and claims the benefit of Japanese Patent Application 2008-172797, filed on Jul. 1, 2008.

TECHNICAL FIELD

The present invention relates to a technique for simultaneously and efficiently culturing antigen-specific CTLs and γδT cells effective in cancer treatment. In addition, the present invention relates to the pharmaceutical use of the cells cultured with the culture technique.

BACKGROUND ART

Recently, immuno-cell therapy is focused as a new therapy for intractable diseases including cancer. The immuno-cell therapy is to collect and activate patient's own immunocytes, particularly white blood cells before returning them to the patient to artificially enhance the immunizing power. This therapy has the advantage of reduced side effects compared to conventional anticancer drug treatment and the like.

As the immuno-cell therapy, activated autologous lymphocyte therapy is already becoming available which involves antigen-non-specifically activating lymphocytes in vitro with a lymphokine and then returning them into the body; however, there is need for the availability of therapy using cytotoxic T lymphocytes (hereinafter referred to as CTLs) which have stronger cytotoxic activity and specifically recognize and injure a lesion.

Here, as currently attempted therapy using CTLs, a method is adopted, for example, which involves directly administering a cancer antigen peptide or the like to a patient; however, in this case, the ability thereof to induce CTLs admits of improvement because the patient often has lowered immunity. Accordingly, there is dendritic cell vaccine therapy or the like which involves contacting an antigen with antigen presentation cells, for example, dendritic cells (hereinafter also referred to as DCs), or the like and thereby strongly causing the cells to present the antigen to induce disease antigen specific CTLs by the DCs in the body.

Some current typical methods for inducing disease antigen specific CTLs are shown below as examples.

For example, in Non Patent Literatures 1 and 2, 9-mer peptides such as an epitope for a particular disease antigen are added to peripheral blood mononuclear cells to attempt the induction of CTLs from there. In addition, in Non Patent Literatures 3 and 4, DCs are obtained from peripheral blood mononuclear cells and an antigen peptide is added thereto to impart an antigen-presenting function; CD8-positive T cells separated from peripheral blood lymphocytes are cultured together with the resultant DCs to induce CTLs specific for the disease antigen.

Further, in Non Patent Literature 5, DC vaccination is carried out using DCs obtained from hematopoietic precursor cells and an antigen peptide and then monocyte-derived DCs to which the antigen is added are co-cultured with CD8-positive T cells separated from peripheral blood mononuclear cells to induce CTLs specific for the antigen.

As can be seen from their use in the above examples, dendritic cells are high in antigen-presenting capability and in the ability to induce disease antigen specific CTLs among other antigen-presenting cells; thus, technological development for obtaining them is under way.

However, to obtain dendritic cells for dendritic cell vaccination, it is typically necessary to collect human peripheral blood, separate cells called monocytes from there, and culture them after adding IL-4, GM-CSF and the like. This process is cumbersome and at present has a problem that the number and function of cultured cells vary depending on the skill of a cell culture technician.

γδT cells, which are activated by a non-peptide antigen, are cells responsible for natural immunity; these cells have recently been found to exert MHC-unrestricted cytotoxic activity (non-specific activity) on cancer cells. Thus, immunotherapy using the strong anti-tumor activity of these γδT cells is investigated.

Because γδT cells are activated by recognizing a non-peptide antigen, they can be stimulated, for example, with an alkylamine or a bisphosphonate as the non-peptide antigen for activation and/or proliferation; γδT cells separated from peripheral blood have been caused to recognize the non-peptide antigen in vitro to perform studies on the activation and/or proliferation thereof (for example, Non Patent Literature 6).

However, a problem of γδT cells, which are generally present in an amount of only 1 to 5% in peripheral blood, is that the purity and number of the γδT cells sufficient for medical treatment cannot be secured even if a small amount of blood is collected and then the cells therefrom are activated and/or proliferated. Increasing the amount of blood collection from a patient to secure the purity and number of the γδT cells sufficient for medical treatment also poses a problem that it imposes a great burden on the patient.

Patent Literature 1 also discloses a method which involves adding a bisphosphonate to peripheral blood mononuclear cells to activate and/or proliferate γδT cells.

Thus the culture and use of more effective cells are very important for immuno-cell therapy; the development of a wide variety of methods and techniques are still carried out.

In addition, one type of cells are mostly cultured under present conditions and used for medical treatment in immuno-cell therapy; however, various cells may probably be mixed and used for medical treatment, given such characteristics that as described above, for example, disease antigen specific CTLs attack targeted cells or tissue in an MHC-restricted manner, for example, specifically for an antigen presented in MHC class I and γδT cells attack cells or tissue in an MHC-unrestricted manner.

However, to culture a plurality of types of immune cells for medical treatment, culture steps had to be concurrently carried out for a number of the types in practice. Culture conditions suitable for each type of cells are different from those for the other; if a conventional culture method suited for one type of cells is used, it will be very difficult, for example, to simultaneously and efficiently culture sufficient numbers of disease antigen specific CTLs and γδT cells for exerting a therapeutic effect; and such effective culture and induction methods are not yet brought to perfection.

CITATION LIST

Patent Literature

Patent Literature 1: WO 2006/006720

Non Patent Literature

Non Patent Literature 1: Sugiyama H. et al. Cancer Immunol. Immunother. December 2002; 51 (11-12):614-20. Epub Oct. 18, 2002.

Non Patent Literature 2: Appella E. et al. J. Immunol. Mar. 1, 1995; 154 (5):2257-65.

Non Patent Literature 3: Fujita S. et al. Blood Jan. 1, 2000; 95 (1):286-93.

Non Patent Literature 4: Yasukawa M. et al. Clin. Cancer Res. August 2002; 8 (8):2626-31.

Non Patent Literature 5: Palucka A K. et al. J. Exp. Med. Jun. 7, 2004; 199 (11):1503-11. Epub Jun. 1, 2004.

Non Patent Literature 6: Fumi Miyagawa et al. The Journal of Immunology 2001; 166 (9):5508-5514.

SUMMARY OF INVENTION

Technical Problem

Made in view of the above-described circumstances, the present invention has an object of simultaneously and efficiently inducing and culturing sufficient numbers of disease antigen specific CTLs and γδT cells for exerting a therapeutic effect in one-step culture.

Solution to Problem

The present inventors have carried out various studies for solving these problems and have created the present invention. The present invention is as follows:

(1) A method for simultaneous induction of disease antigen specific CTLs and γδT cells, characterized by comprising the steps of: adding a disease antigen and an aminobisphosphonate to peripheral blood and culturing the resultant peripheral blood; (2) The method for simultaneous induction of disease antigen specific CTLs and γδT cells according to item (1), wherein the step of adding a disease antigen and an aminobisphosphonate is carried out on the first day of culture; (3) The method for simultaneous induction disease antigen specific CTLs and γδT cells according to item (1) or (2), wherein the aminobisphosphonate is pamidronic acid, alendronic acid, zoledronic acid, risedronic acid, ibandronic acid, incadronic acid, a salt thereof and/or a hydrate thereof; (4) The method for simultaneous induction of disease antigen specific CTLs and γδT cells according to any one of items (1) to (3), wherein the disease antigen is a cancer antigen; (5) The method for simultaneous induction of disease antigen specific CTLs and γδT cells according to any one of items (1) to (4), wherein the disease antigen and the aminobisphosphonate are simultaneously added; (6) A pharmaceutical agent comprising disease antigen specific CTLs and γδT cells obtained by the method according to any one of items (1) to (5); and (7) A therapeutic/prophylactic method comprising administration of disease antigen specific CTLs and γδT cells obtained by the method according to any one of items (1) to (5).

As a result of studies, the present inventors have found that γδT cells in peripheral blood activated by an aminobisphosphonate are proliferated and these activated and proliferated γδT cells exhibit a function as APCs (antigen presenting cells) to present a disease antigen and also promote the induction of disease antigen specific CTLs, thereby accomplishing the present invention.

Advantageous Effects of Invention

In conventional methods for culturing and inducing disease antigen specific CTLs and γδT cells, the desired cells have been obtained through various steps and then started to be cultured; however, the present invention can provide disease antigen specific CTLs and γδT cells simultaneously and efficiently in one-step culture without separation of the cells from peripheral blood and even a cell population containing a large number of cells excellent in therapeutic effect. The mixed cell population of disease antigen specific CTLs and γδT cells obtained by this induction method enables the provision of medical treatment having a higher effect than conventional medical treatment by administering single immune cells as a pharmaceutical agent.

Particularly, the induction of CTLs has previously required the steps of: (1) separating mononuclear cells from blood; (2) adding a cytokine to induce dendritic cells; (3) pulsing the dendritic cells with an antigen; and (4) co-culturing the antigen-pulsed dendritic cells and lymphocytes to induce CTLs. However, the use of the present invention enables the omission of the step of inducing dendritic cells, which can reduce workload, can also decrease the risk of contamination, and can further shorten the period (about 7 days) during which the dendritic cells are induced.

DESCRIPTION OF EMBODIMENTS

Embodiments of the present invention will be described below.

First Embodiment

Method for Simultaneously Inducing Disease Antigen Specific CTLs and γδT Cells According to the Present Invention The method for simultaneously inducing disease antigen specific CTLs and γδT cells according to the present invention (hereinafter also simply referred to as "the induction method of the present invention") is characterized by comprising the steps of: adding a disease antigen and an aminobisphosphonate to peripheral blood and culturing the resultant peripheral blood.

While it has conventionally been very difficult to obtain disease antigen specific CTLs and γδT cells in such amounts as to be effective in medical treatment in the same culture step, the induction method of the present invention enables these types of cells to be simply obtained with high efficiency by passing through the above steps.

According to the induction method of the present invention, γδT cells in peripheral blood are activated by an aminobisphosphonate and proliferated and these activated and proliferated γδT cells also exhibit a function as APCs to present a disease antigen and induce disease antigen specific CTLs. In addition, the γδT cells having a function as APCs not only act simply as APCs, but also continue to be still proliferated even after the proliferation of disease antigen specific CTLs, enabling sufficient numbers of both types of cells for exerting a therapeutic effect to be obtained.

Specific procedures of the induction method of the present invention will be described below.

1) Blood is collected to provide peripheral blood. The amount thereof required is 15 to 25 mL. Such a amount enables the blood to be suitably cultured. However, a sufficient amount of the peripheral blood at the start of culture is not limited to the range, and because a larger amount of blood collection increases the number of collected disease antigen specific CTLs and γδT cells, a larger amount of blood is preferably collected provided that the burden placed on the donor from which the blood is collected is low.

2) Peripheral blood mononuclear cells are obtained, for example, by a density gradient centrifugation. The number of the peripheral blood mononuclear cells which can be obtained is about 1 to $2\times10^7$ from 5 to 25 mL of peripheral blood.

3) The peripheral blood mononuclear cells obtained in 2) are suspended in a culture medium, AIM-V (Invitrogen). Here, a solution in which the peripheral blood mononuclear cells are suspended is referred to as a cell suspension. Besides the culture medium described above, a commercially available culture medium used for cell culture may be used such as RPMI-1640 medium (Invitrogen), Dulbecco's Modified Eagle medium (Invitrogen; hereinafter referred to as DMEM), or Iscove's medium (Invitrogen; hereinafter referred to as IMEM).

4) The cell suspension obtained in 3) is seeded in a flask, a bag, or a plate.

5) An aminobisphosphonate is added to a concentration of 0.05 to 100 μM, preferably 0.1 to 30 μM to the peripheral blood mononuclear cells seeded in the flask, bag, or plate.

Here, the bisphosphonate is an analog of pyrophosphoric acid and is a compound in which the O (oxygen atom) of the pyrophosphoric acid skeleton P—O—P is substituted with C (carbon atom) (P—C—P). It is generally used as a therapeutic drug for osteoporosis. The aminobisphosphonate refers to a compound having N (nitrogen atom) among the bisphosphonates. For example, the aminobisphosphonate used in the present invention is not particularly limited; aminobisphosphonates and the like as disclosed in WO 2006/006720 and WO 2007/029689 may be used. Specific examples thereof include pamidronic acid, its salt and/or their hydrate, alendronic acid, its salt and/or their hydrate, and zoledronic acid, its salt and/or their hydrate. The concentration of the aminobisphosphonates is preferably 1 to 30 μM for pamidronic acid, its salt and/or their hydrate, 1 to 30 μM for alendronic acid, its salt and/or their hydrate, and 0.1 to 10 μM for zoledronic acid, its salt and/or their hydrate. Here, 5 μM zoledronic acid is added as an example.

6) When the aminobisphosphonate is added in 5), a disease antigen is added together therewith. Here, the "disease" is, for example, cancer or infection. The cancer is not particularly limited and includes any cancer; examples thereof include cancers difficult to treat. Examples of the infection include viral infection such as AIDS or hepatitis B or C, cell infection, bacterial infection, fungal infection, or protozoan infection.

As a form of the antigen, a peptide, a protein, or the like may be used as needed. Lysate of cancer or infected cells, apoptotic cells, necrotic cells, heat-treated products thereof, and the like may be used.

The antigen may be one derived from a patient (for example, a tumor tissue or the like isolated by surgery from a patient) or a synthesized one. The use of a synthetic peptide can reduce the burden of a patient compared to the use of a cancer antigen harvested from the patient's own cancer tissue or the like.

The addition amount may be of the order of 0.02 to 2 μg/ml for a peptide. For example, 2 μg/ml is added.

The order in which the aminobisphosphonate and the disease antigen are added is not particularly limited, and both may be added simultaneously or either of them may be added earlier; however, the simultaneous addition is preferable.

6) In addition, IL-2 is added to a concentration of 50 to 2,000 U/mL, more preferably 400 to 1,000 U/mL, to the above culture medium.

7) After addition of IL-2, culture is performed at 34 to 38° C., more preferably 37° C. in the presence of 2 to 10%, more preferably 5% $CO_2$. On this occasion, a culture medium is properly added depending on the number of cultured cells. In addition, IL-2 is properly added to a concentration of 50 to 2,000 U/mL, more preferably 400 to 1,000 U/mL with increasing culture medium.

8) Further, serum is added in an amount of 0.1 to 20% to the above culture solution. As the serum, fetal calf serum (hereinafter referred to as FCS), AB serum, or auto-plasma may be used, for example.

In this manner, when the culture period is 7 days or more, a cell group comprising disease antigen specific CTLs and γδT cells is obtained with high purity; however, the culture is preferably performed for about 14 days to further increase the number of cells.

Plasma is also preferably added to the culture solution during the above culture step. The addition time ranging roughly from 0 to 100 hours after the start of culture enables the culture to be satisfactorily performed.

Second Embodiment

Pharmaceutical Agent Comprising Disease Antigen Specific CTLs and γδT Cells

The pharmaceutical agent of the present invention is a pharmaceutical agent comprising disease antigen specific CTLs and γδT cells, the agent being obtained by adding a disease antigen and an aminobisphosphonate to peripheral blood at the beginning of culture for culture.

A conventional immuno-cell therapy has used a single type of cells, or used a plurality of types of cells by adding these types of separately cultured cells after mixing them at the time of administration or simultaneously.

In contrast, the pharmaceutical agent of the present invention is obtained by simultaneously culturing disease antigen specific CTLs and γδT cells by the induction method of the present invention, which enables a large number of cells to be very simply obtained. The use of such a pharmaceutical agent has an advantage that it provides a higher therapeutic efficacy than that for the conventional use of a single type of immune cells because of the synergistic effect between the disease antigen specific CTLs and the γδT cells.

The pharmaceutical agent of the present invention will be specifically described below.

1) The cells obtained by the culture method of the present invention are collected by a centrifugation or the like.

2) The collected cells are washed with a washing solution. The washing solution is preferably an isotonic solution having the same osmotic pressure as that of the cells and more preferably a liquid capable of being used as a medicine. Here, considering that it is administered to patients, saline or PBS (phosphate buffered saline) is preferable, for example.

3) A lymphocyte population predominantly containing disease antigen specific CTLs and γδT cells obtained after washing can be collected by a centrifugation or the like and suspended in a liquid usable as a medicine, for example, saline to prepare the pharmaceutical agent of the present invention. Here, the usage amount of the liquid for suspension is properly adjusted depending on the number of cells administered and the administration method.

In the lymphocyte population predominantly containing disease antigen specific CTLs and γδT cells used in the pharmaceutical agent of the present invention, the number of the cells is properly selected depending on the administration method, the type of disease, the pathology of a patient, and the like; however, it is typically preferably $10^8$ to $10^{12}$/person, more preferably $10^9$/person or more.

4) Subsequently, these are suspended in saline to provide the pharmaceutical agent of the present invention. The pharmaceutical agent of the present invention can be used as a therapeutic/prophylactic agent for cancer or infection.

Here, in the case of use as a therapeutic/prophylactic agent for cancer, the pharmaceutical agent of the present invention can also be combined with a cytokine such as IL-2 or IL-12.

In the case of use as therapeutic/prophylactic agent for viral infection, the pharmaceutical agent of the present invention can also be combined with interferon-γ (IFN-γ) or the like.

5) The administration method may be for example intravenous, intradermal or subcutaneous injection, direct injection into a lesion, or systemic administration by drip infusion. In addition, it may be injection through an artery in the vicinity of a lesion.

Third Embodiment

Therapeutic/Prophylactic Method Involving Administering Disease Antigen Specific CTLs and γδT Cells The therapeutic/prophylactic method of the present invention is a therapeutic/prophylactic method which involves administering disease antigen specific CTLs and γδT cells obtained by adding a disease antigen and an aminobisphosphonate to peripheral blood at the beginning of culture for culture.

The therapeutic/prophylactic method of the present invention will be specifically described below.

1) Cells obtained by the culture method of the present invention are collected by a centrifugation or the like.

2) The collected cells are washed with a washing solution. The washing solution is preferably an isotonic solution having the same osmotic pressure as that of the cells and more preferably a liquid capable of being used as a medicine. Here, considering that it is administered to patients, saline or PBS (phosphate buffered saline) is preferably used, for example.

3) A lymphocyte population predominantly containing disease antigen specific CTLs and γδT cells obtained after washing can be collected by a centrifugation or the like and suspended in a liquid usable as a medicine, for example, saline to prepare a cell suspension used in the therapeutic/prophylactic method of the present invention. Here, the usage amount of the liquid for suspension is properly adjusted depending on the number of cells administered and the administration method.

In the lymphocyte population predominantly containing disease antigen specific CTLs and γδT cells used in the therapeutic/prophylactic method of the present invention, the number of the cells is properly selected depending on the administration method, the type of disease, the pathology of a patient, and the like; however, it is typically preferably $10^8$ to $10^{12}$/person, more preferably $10^9$/person or more.

4) Subsequently, these are suspended in saline to provide a cell suspension.

Here, in the case of treating or preventing cancer, the pharmaceutical agent of the present invention can also be combined with a cytokine such as IL-2 or IL-12.

In the case of treating or preventing viral infection, the pharmaceutical agent of the present invention can also be combined with interferon-γ (IFN-γ) or the like.

5) The administration method may be for example intravenous, intradermal or subcutaneous injection, direct injection into an affected area, or systemic administration by drip infusion. In addition, it may be injection through an artery in the vicinity of an affected area.

The present invention will be described below in detail with reference to Examples. However, it is to be understood that the present invention is not intended to be limited thereto.

Example 1

Culture/Induction Method of Present Invention

1) Peripheral blood (42 ml) was collected from a healthy donor and peripheral blood mononuclear cells were separated therefrom using a density gradient solution for blood cell separation.

2) The resultant peripheral blood mononuclear cells were suspended in AIM-V.

3) These peripheral blood mononuclear cells ($8 \times 10^6$/4 mL) were seeded in a 6-well plate (SUMILON). Thereto was added 1,000 U/mL IL-2, to which 5 μM zoledronic acid (ZOMETA (trade name)) and 2 μg/ml Mart-1 (A27L, sequence: ELAGIGILTV) as a peptide were further added, followed by starting culture under conditions of 37° C. and 5% $CO_2$ concentration.

4) In addition, AB serum was added in an amount of 10% after starting the culture.

5) AIM-V containing 1,000 U/ml IL-2 and AB serum were added depending on the proliferation of cells, which were then cultured for 14 days.

6) In the cell population obtained after culture for 7 days or 14 days as described above, the percentage of disease antigen specific CD8-positive T cells and the percentage of cells expressing TCRVγ9 were measured using an anti-CD8 antibody (BD Pharmingen), T-Select HLA-A*0201 Mart-1 Tetramer ELAGIGILTV (MBL), an anti-TCRVγ9 antibody (Beckman Coulter) and an anti-CD3 antibody (Beckman Coulter) with a fluorescence-activated cell sorter (hereinafter referred to as FACS; Epics XL-MCL ADC, Beckman Coulter). The values obtained by the measurement are shown as follows.

TABLE 1

Percentage (%) of Disease Antigen Specific CD8-Positive T Cells Contained in Mononuclear Cells at Day 7 and Day 14 of Culture

| | Number of Days in Culture | | | |
|---|---|---|---|---|
| | 7 Days | | 14 Days | |
| Disease Antigen | − | + | − | + |
| Donor: A | 0.00 | 0.41 | 0.00 | 0.36 |
| Donor: B | 0.01 | 0.26 | 0.00 | 0.09 |
| Donor: C | 0.02 | 0.14 | 0.00 | 0.10 |

TABLE 2

Percentage (%) of γδT Cells Contained in Mononuclear Cells at Day 7 and Day 14 of Culture

| | Number of Days in Culture | | | |
|---|---|---|---|---|
| | 7 Days | | 14 Days | |
| Disease Antigen | − | + | − | + |
| Donor: A | 43.7 | 41.9 | 80.9 | 80.6 |
| Donor: B | 68.2 | 62.6 | 99.0 | 99.5 |
| Donor: C | 28.6 | 26.8 | 89.2 | 85.7 |

TABLE 3

Expansion Fold (times) of Disease Antigen Specific CD8-Positive T Cells Contained in Mononuclear Cells at Day 7 and Day 14 of Culture

|  | Number of Days in Culture | | | |
|---|---|---|---|---|
|  | 7 Days | | 14 Days | |
| Disease Antigen | − | + | − | + |
| Donor: A | 0.00 | 74.46 | 0.00 | 2495.68 |
| Donor: B | 1.79 | 31.42 | 0.00 | 343.73 |
| Donor: C | 0.57 | 4.31 | 0.00 | 151.88 |

TABLE 4

Expansion Fold (times) of γδT Cells Contained in Mononuclear Cells at Day 7 and Day 14 of Culture

|  | Number of Days in Culture | | | |
|---|---|---|---|---|
|  | 7 Days | | 14 Days | |
| Disease Antigen | − | + | − | + |
| Donor: A | 50.40 | 42.28 | 4027.31 | 3104.19 |
| Donor: B | 31.31 | 19.40 | 1328.85 | 974.39 |
| Donor: C | 4.97 | 5.00 | 1244.02 | 786.25 |

The above results confirmed that a lymphocyte population predominantly containing disease antigen specific CD8-positive T cells (CTLs) and γδT cells was obtained by simultaneously adding a disease antigen and an aminobisphosphonate for culture.

Example 2

Study of Effect of Addition of Disease Antigen on Expression Ratio of CD56 on γδT Cells Whether the addition of a disease antigen affects the expression ratio of CD56 on γδT Cells or not was examined by the following procedures. CD56 is an isoform of a neural cell adhesion molecule (N-CAM) and an adhesion factor known as a marker for NK cells. It is one of the markers providing indicators of the cytotoxic activity of γδT cells.

1) Peripheral blood (8 ml) was collected from a healthy donor and peripheral blood mononuclear cells were separated therefrom using a density gradient solution for blood cell separation.

2) The resultant peripheral blood mononuclear cells were suspended in AIM-V.

3) These peripheral blood mononuclear cells ($1.8 \times 10^6/25$ mL) were seeded in a 12-well plate (SUMILON). Thereto was added 1,000 U/mL IL-2, to which 5 μM zoledronic acid (ZOMETA) and 2 μg/ml Mart-1 (A27L) as a peptide were further added, followed by starting culture under conditions of 37° C. and 5% $CO_2$ concentration.

4) In addition, AB serum was added in an amount of 10% after starting the culture.

5) AIM-V containing 1,000 U/ml IL-2 and AB serum were added depending on the proliferation of cells, which were then cultured for up to 14 days.

6) In the cell population obtained after culture for up to 14 days as described above, the percentage of cells expressing TCRVγ9 or the percentage of cells expressing CD-56 were measured using an anti-TCRVγ9 antibody (Beckman Coulter), an anti-CD56 antibody (Beckman Coulter) and an anti-CD3 antibody (Beckman Coulter) with FACS (Epics XL-MCL ADC, Beckman Coulter). The values obtained by the measurement are shown in Table 5.

TABLE 5

Surface Antigen Expression Ratio (%) of γδT Cells Contained in Mononuclear Cells at Day 13 of Culture

|  |  | Expression Ratio (%) | |
|---|---|---|---|
| Gate Area | Surface Antigen | Disease Antigen (−) | Disease Antigen (+) |
| Live Cells | CD3 | 98.5 | 98.4 |
|  | Vγ9-TCR | 97.0 | 96.5 |
|  | CD56 | 54.4 | 51.2 |
| CD3 | CD56 | 53.1 | 49.9 |
| Vγ9 | CD56 | 53.1 | 49.6 |

As shown in Table 5, no difference was observed in the expression ratio of the surface antigen on γδT cells between a case where the disease antigen is not added (−) and a case where the antigen was added (+), confirming that the addition of the disease antigen did not have a large influence on the CD56 expression ratio of γδT cells.

INDUSTRIAL APPLICABILITY

As described above, the method for simultaneously inducing disease antigen specific CTLs and γδT cells according to the present invention enables the proliferation and induction of both types of cells to the number of cells allowing each type of cells to exert a therapeutic effect in one blood collection whereas the disease antigen specific CTLs and γδT cells have been separately cultured in conventional methods. This enables both disease specific and non-specific immune cells to be simultaneously and simply used for medical treatment, which can improve a therapeutic effect thereof and reduce burden on patients. In addition, its advantage can also be enjoyed in terms of economical aspects such as culture cost because culture steps can be unified into one step.

The invention claimed is:

1. A method for simultaneous proliferation of disease antigen specific cytotoxic T lymphocytes (CTLs) and γδT cells, the method consisting of:
    adding a disease antigen and an aminobisphosphonate to isolated peripheral blood; and
    culturing the resultant combination consisting of isolated peripheral blood, the disease antigen and the aminobisphosphonate in a culture media.

2. The method for simultaneous proliferation of disease antigen specific CTLs and γδT cells according to claim 1, wherein the aminobisphosphonate is pamidronic acid, alendronic acid, zoledronic acid, risedronic acid, ibandronic acid, incadronic acid, a salt thereof and/or a hydrate thereof.

3. The method for simultaneous proliferation of disease antigen specific CTLs and γδT cells according to claim 1, wherein the disease antigen is a cancer antigen.

4. The method for simultaneous proliferation of disease antigen specific CTLs and γδT cells according to claim 1, wherein the disease antigen and the aminobisphosphonate are simultaneously added.

5. A method for simultaneous proliferation of disease antigen specific cytotoxic T lymphocytes (CTLs) and γδT cell, the method consisting of:
    adding a disease antigen and an aminobisphosphonate to an isolated mononuclear cell fraction of peripheral blood; and culturing the resultant combination consisting of isolated peripheral blood, the disease antigen and the aminobisphosphonate in a culture media.

6. The method for simultaneous proliferation of disease antigen specific CTLs and γδT cells according to claim 5, wherein the aminobisphosphonate is pamidronic acid, alendronic acid, zoledronic acid, risedronic acid, ibandronic acid, incadronic acid, a salt thereof and/or a hydrate thereof.

7. The method for simultaneous proliferation of disease antigen specific CTLs and γδT cells according to claim 5, wherein the disease antigen is a cancer antigen.

8. The method for simultaneous proliferation of disease antigen specific CTLs and γδT cells according to claim 5, wherein the disease antigen and the aminobisphosphonate are simultaneously added.

9. The method according to claim 5, wherein the culture media comprises added-interleukin-2 (IL-2).

10. The method according to claim 5, wherein the culture media comprises serum and/or plasma.

11. A method for simultaneous proliferation of disease antigen specific cytotoxic T lymphocytes (CTLs) and γδT cells, the method comprising:
culturing a combination of isolated peripheral blood, a disease antigen and an aminobisphosphonate in a culture media
without a separate culture step of in vitro induction of monocyte-derived dendritic cells from mononuclear cells.

12. The method according to claim 11, wherein the aminobisphosphonate is pamidronic acid, alendronic acid, zoledronic acid, risedronic acid, ibandronic acid, incadronic acid, a salt thereof and/or a hydrate thereof.

13. The method according to claim 11, wherein the disease antigen is a cancer antigen.

14. A method for simultaneous proliferation of disease antigen specific cytotoxic T lymphocytes (CTLs) and γδT cells, the method comprising:
culturing a combination an of an isolated mononuclear cell fraction of peripheral blood, a disease antigen and an aminobisphosphonate in a culture media
without a separate culture step of in vitro induction of monocyte-derived dendritic cells from mononuclear cells.

15. The method according to claim 14, wherein the aminobisphosphonate is pamidronic acid, alendronic acid, zoledronic acid, risedronic acid, ibandronic acid, incadronic acid, a salt thereof and/or a hydrate thereof; and the disease antigen is a cancer antigen.

16. The method according to claim 14, wherein the culture media comprises IL-2, and serum and/or plasma.

* * * * *

UNITED STATES PATENT AND TRADEMARK OFFICE
CERTIFICATE OF CORRECTION

| | | |
|---|---|---|
| PATENT NO. | : 8,962,313 B2 | Page 1 of 1 |
| APPLICATION NO. | : 13/001581 | |
| DATED | : February 24, 2015 | |
| INVENTOR(S) | : Mie Nieda, Mai Tomiyama and Masato Muto | |

It is certified that error appears in the above-identified patent and that said Letters Patent is hereby corrected as shown below:

In the Claims

In Column 11, line 18, Claim 9, please remove -- added- -- before "interleukin-2 (IL-2)."

Signed and Sealed this
Ninth Day of June, 2015

Michelle K. Lee
*Director of the United States Patent and Trademark Office*